(12) United States Patent
Aygen

(10) Patent No.: US 10,266,872 B2
(45) Date of Patent: Apr. 23, 2019

(54) METHOD FOR ISOLATING UREA WHILE REMOVING OBJECTIONABLE CO2

(75) Inventor: Sitke Aygen, Cologne (DE)

(73) Assignee: Cytonet GmbH & Co. KG, Weinheim (DE)

( * ) Notice: Subject to any disclaimer, the term of this patent is extended or adjusted under 35 U.S.C. 154(b) by 90 days.

(21) Appl. No.: 13/817,995

(22) PCT Filed: Jul. 30, 2011

(86) PCT No.: PCT/EP2011/003837
§ 371 (c)(1),
(2), (4) Date: Feb. 20, 2013

(87) PCT Pub. No.: WO2012/022428
PCT Pub. Date: Feb. 23, 2012

(65) Prior Publication Data
US 2013/0149727 A1    Jun. 13, 2013

(30) Foreign Application Priority Data

Aug. 20, 2010 (EP) ..................... 10173593
Dec. 7, 2010 (EP) ..................... 10193920

(51) Int. Cl.
*C12Q 1/58* (2006.01)
*G01N 33/62* (2006.01)
(52) U.S. Cl.
CPC ............. *C12Q 1/58* (2013.01); *G01N 33/62* (2013.01)
(58) Field of Classification Search
CPC ................... F26B 5/06; C12Q 1/68

USPC .......................................... 435/12
See application file for complete search history.

(56) References Cited

U.S. PATENT DOCUMENTS

| 4,188,465 A | | 2/1980 | Schneider et al. |
| 4,477,575 A | * | 10/1984 | Vogel ............ B01D 39/2017 210/509 |
| 5,542,419 A | | 8/1996 | Moulton-Barrett |

(Continued)

FOREIGN PATENT DOCUMENTS

| EP | 1 415 159 | 5/2004 |
| JP | 55-069038 | 5/1980 |
| RU | 2122740 | 11/1998 |

(Continued)

OTHER PUBLICATIONS

Mendel Tuchman, et al.; "N-carbamylglutamate Markedly Enhances Ureagenesis in N-acetylglutamate Deficiency and Propionic Acidemia as Measured by Isotopic Incorporation and Blood Biomarkers", Pediatric Research, Williams and Wilkins, Baltimore, MD, US, Bd. 64, Nr. 2, Aug. 1, 2008, pp. 213-217, XP008127178.

(Continued)

*Primary Examiner* — Erin M. Bowers
(74) *Attorney, Agent, or Firm* — Norris McLaughlin, P.A.

(57) ABSTRACT

A method for isolating urea and removing $CO_2$ from plasma samples, comprising the following steps: a) providing a plasma sample; b) adding an acid so as to partially remove $CO_2$; c) lyophilizing the sample so as to further remove $CO_2$ and obtain a dried sample; and d) redissolving the dried sample and neutralizing to a pH value of 4 to 7 using a buffer solution, wherein optionally a filtration step is carried out before adding the acid.

9 Claims, 6 Drawing Sheets

(56) References Cited

U.S. PATENT DOCUMENTS

2008/0090268 A1  4/2008  Aygen
2009/0113753 A1* 5/2009  Pepper et al. .................. 34/284

FOREIGN PATENT DOCUMENTS

SU         743600       6/1980
WO    WO-2006/028648   3/2006

OTHER PUBLICATIONS

W. D. Chey, et al.; "The $^{13}$C-Urea Blood Test Accurately Detects Active *Helicobacter pylori* Infection: A United States, Multicenter Trial", American Journal of Gastroenterology, Elsevier Science Inc, US, Bd. 94, Nr. 6, Jan. 1, 1999. pp. 1522-1524, XP002245806.
"Isotope ratio mass spectrometry"; Wikepedia, http://en.wikipedia.org/w/index.php?title=Isotope_ratio_mass_spec, Sep. 21, 2010, XP002601660.

* cited by examiner

METHOD FOR ISOLATING UREA WHILE REMOVING OBJECTIONABLE CO2

BACKGROUND OF THE INVENTION

The present invention relates to a method for isolating urea present in blood samples.

Urea is an organic compound, which constitutes an end product of the metabolism of nitrogen compounds in the human organism. In humans, urea is excreted with the urine.

Urea is primarily produced in liver cells and to a lesser extent in the kidneys. The production of urea in the body is associated with a variety of diseases, some of them congenital, which can cause significant damage to a person's health. Determining the production of urea is an indicator of the function of the liver, for example during liver transplants or the transplantation of liver cells.

For example, on page 213, Tuchman et al., Pediatric Research 2008 (64), describe a deficiency of N-acetylglutamate synthase and the analysis of urea production.

So as to measure the production of urea, patients were orally administered $^{13}C$-labeled sodium-acetate, which in the body resulted in the production of $^{13}C$-labeled urea; $^{13}C$-labeled acetate turns into $^{13}CO_2$, which is converted to $^{13}C$ carbamoyl-phosphate and then to $^{13}C$ urea.

The majority of chemical elements exist in nature in form of mixtures of several stable or radioactive isotopes. Even in tracer studies using enriched compounds, isotopic abundance is generally indicated using the unit atom percent (atom %) or ppm. The relative delta scale in parts per thousand (‰) exists to describe the variations in the range of natural abundance. The δ values (such as $\delta^{13}C$, $\delta^{15}N$, $\delta^{18}O$) are defined as the difference of the respective isotope ratio R ([heavy isotope]/[light isotope], for example $R^{13}C=[^{13}C]/[^{12}C]$) of the sample compared to a standard, relative to this standard.

For example, the $\delta^{13}C$ value is calculated as follows:

$$\delta^{13}C = \frac{R_{sample} - R_{Standard}}{R_{Standard}} \cdot 1000 = \left(\frac{R_{sample}}{R_{Standard}} - 1\right) \cdot 1000$$

The standard for carbon is limestone, Pee Dee Belemnite (PDB). The carbon that is bound by inserting $CO_2$ in the photosynthesis is generally depleted of $^{13}C$. The majority of plants reduce $CO_2$ to form carbohydrates according to the Calvin-Benson or C3 pathway. This causes the biomass of C3 plants (which include the useful plants rice, potatoes, soy, sugar beets, and cereals) to show $\delta^{13}C$ values in the range of −24 to −32‰. Other plants fix $CO_2$ according to the Hatch-Slack or C4 pathway. The $\delta^{13}C$ values of products from C4 plants (corn, millet, and sugar cane) have $\delta^{13}C$ values in the range of −10 to −16‰. This allows $\delta^{13}C$ values to be used to check the origin and uniqueness of organic substances.

The $\delta^{13}C$ value of plasma urea is usually determined by way of reacting urea to form $CO_2$ using an enzyme. Therefore, it is important that the urea solution that is isolated from plasma is free of foreign $CO_2$. However, $CO_2$ is generally always present in the plasma, either as dissolved free $CO_2$ or as bound $CO_2$ in the form of bicarbonate. Freeing the plasma entirely from $CO_2$ is not easy to do; in addition, $CO_2$ must be prevented from being introduced in the sample during the isolation.

Tuchman et al. employ a method comprising the following steps to isolate the urea from blood plasma:

A plasma sample of 0.5 ml was mixed with 0.5 ml $H_2O$ and 40 μl 60% perchloric acid, and precipitated protein was separated. Thereafter, the container rested for 30 minutes so as to allow $CO_2$ to be released. After transferring the mixture to a new vessel and adjusting the pH to the range of 6 to 7 using 300 μl KOH 1 M, precipitated potassium perchlorate was separated. The remaining bicarbonate was removed using an ion exchange column.

The column was washed with 1 ml HCl 10 mM and the eluate was dried in a glass container at 80° C. The sample rested overnight in a closed container in which also a piece of gauze, which was saturated with sodium hydroxide, was enclosed so as to absorb residues of $CO_2$.

Thereafter, the container was rinsed with helium and the vessel was closed in an air-tight manner with a rubber stopper. An amount of 400 μl potassium phosphate buffer 0.5 M, pH 6.0, containing 3 mg urease enzyme/400 μl was injected through the rubber stopper. After one hour, 100 μl 20% phosphoric acid was added so as to release $CO_2$ and stop the urease reaction. The released $^{13}CO_2$ was measured using an isotope ratio mass spectrometer (IRMS).

SUMMARY OF THE INVENTION

The analyses conducted by the applicant showed that the method described above is very sensitive. With this method, several sources of foreign $CO_2$ can distort the measured delta values of the $CO_2$ that resulted from urea. In addition, the method is also extremely complex and protracted. Because of the low yield of urea, a larger volume (0.5 ml) of plasma is necessary. This may cause problems in children. In addition, non-reproducible differences were shown in the results of a cross-validation conducted with the USA and Europe.

A comparison of the $\delta^{13}C$ values of $CO_2$ generated from urea can be used to demonstrate that the method described in Tuchman et al. is not successful in completely eliminating undesirable $CO_2$. The $\delta^{13}C$ values observed by Tuchman et al. are very low at −25 to −26‰.

In plasma, natural urea has a $\delta^{13}C$ value of −19 to −23‰, depending on diet.

It is the object of the invention to provide a method that overcomes at least some of the disadvantages of the known method.

The object is achieved by a method for isolating urea and removing $CO_2$ in plasma samples, comprising the following steps:
 a) providing a plasma sample containing urea;
 b) adding an acid so as to partially remove $CO_2$;
 c) lyophilizing the sample so as to remove $CO_2$ and obtain a dried sample; and
 d) redissolving the dried sample and neutralizing the resulting solution to a pH value of 4 to 7, preferably 4 to 6.9, and in particular 4 to 6, using a buffer solution.

The starting point for the isolation of the urea in a plasma sample is a plasma sample that contains urea. Plasma samples can be obtained in the known manner from blood samples. Because of the high reproducibility of the method according to the invention, plasma samples having a volume in the range of 0.2 to 0.3 ml suffice, however larger quantities can also be used.

At the very least, the plasma sample contains urea having a natural isotope ratio. In addition, the sample can be mixed with urea enriched with $^{13}C$. However, it may also be enriched with $^{13}C$ by administering $^{13}C$-labeled precursors, for example acetate or bicarbonate. Compatible salts thereof, for example Na or K salts, may be administered.

According to the invention, the urea is measured by reacting the urea with urease so as to release $CO_2$, and therefore initially present $CO_2$ must be removed.

In one embodiment of the invention, a filtration step is first carried out. For this purpose, solvent, for example acetonitrile and/or formic acid, is added for precipitation. As a result of this filtration, proteins, and lipids can be separated from the plasma. So-called HybridSPE™ columns, which are available from SUPELCO, are particularly suited for this purpose. In particular, these are also suited for removing phospholipids.

However, in the invention it is also possible to dispense with the step of separating the proteins and lipids from the plasma, still achieving values that can be reproduced very easily. Dispensing with the filtration step saves not only time but also costs, which are incurred for corresponding filters.

According to the invention, an acid is added. Because of the addition of acid, a portion of the $CO_2$ is removed from the plasma sample. For example, phosphoric acid is suitable for this purpose in a concentration of approximately 20%. Relative to a plasma sample of 0.3 ml, a quantity of acid (phosphoric acid, for example) of approximately 50 µl is sufficient. Of course, it is also possible to use other acids.

An essential step of the method according to the invention is the subsequent lyophilization of the sample. Lyophilization is a method in which a sample is frozen and the water contained therein is sublimed under vacuum. According to the invention, this method is excellently suited for removing residual amounts of $CO_2$ in the sample.

The sample thus obtained is then dissolved again and adjusted to a pH value in the range of 4 to 7, preferably 4 to 6.9, in particular 4 to 6, and preferably 5 to 6. Buffer solutions, for example phosphate buffer solutions having a pH of 9.0, are especially suited for adjustment purposes. Other buffer solutions may also be used. The caustic potash solution used in Tuchman et al. is particularly unfavorable because this contains in part larger quantities of $CO_2$.

In one embodiment of the invention, the samples are degassed after the dried samples have been redissolved so as to expel residues of foreign $CO_2$, particularly from the addition of the buffer. Applying a vacuum in the range of 1 to 10 mbar for 2 to 3 hours has been found suitable.

The result of this method is a sample that still contains the urea from the plasma, but is substantially free of $CO_2$ from the plasma.

So as to determine the isotope ratio of the urea, a method that is known per se, this being the conversion using urease, is employed:

The redissolved sample is rinsed with an inert gas, for example helium, nitrogen, or argon, and closed in a gas-tight manner. Thereafter, urease is added so as to produce $CO_2$ from the available urea. Urease, such as that which is available from Sigma for example, is suitable for this purpose. A quantity of 20 to 100 units of urease for a plasma sample of 0.3 ml has been found to be particularly suitable.

Thereafter, the solution is incubated. Incubation at a temperature of approximately 36° C. for a period of approximately 60 minutes has proven to be suitable.

Then, an acid is added so as to stop further urease reaction. The addition of the acid further releases the $CO_2$ that has been produced. With respect to the plasma sample having a volume of 0.3 ml, the use of 100 µl 20% phosphoric acid has proven to be suitable. $CO_2$ that originated from the reaction of the urea in the plasma has now been released in the gas-tight container. The isotope ratio of the $CO_2$ can now be determined. IRMS is especially suited for this determination. With IRMS, the ratio between $^{13}C$ and $^{12}C$ relative to standard is measured, as described above.

So as to check the execution, it may be useful to check whether the solution is free from $CO_2$ before adding urease. This can be done by means of IRMS, for example.

In one application of the invention in order to measure the kinetics of the urea production, the patient is administered $^{13}C$-labeled substances so as to determine the production of $^{13}C$-labeled urea. In a preferred embodiment of the invention, the kinetics is determined by first collecting a blood sample before a patient takes $^{13}C$-labeled urea precursors (basal value), followed by one or preferably more blood collections after the patient has taken $^{13}C$-labeled urea precursors. This allows the production of $^{13}C$-labeled urea to be checked.

According to the invention, plasma volumes of approximately 100 to 200, or 200 to 300 ml can be used, which is to say a blood sample half the size compared to the method according to Tuchman suffices. In particular, when the kinetics is determined and the method is employed in children, it is advantageous if the amounts of collected blood are especially small. Compared to the method according to Tuchman et al., the method according to the invention offers better reproducibility and is less complex.

In a particularly preferred embodiment, the present invention relates to the following aspects:

Aspect 1

A method for isolating urea and removing $CO_2$ from plasma samples, comprising the following steps: a) providing a plasma sample; b) adding an acid so as to partially remove $CO_2$; c) lyophilizing the sample so as to further remove $CO_2$ and obtain a dried sample; and d) redissolving the dried sample and neutralizing the resulting solution to a pH value of 4 to 7, preferably 4 to 6.9, and most preferably 4 to 6, using a buffer solution.

Aspect 2

The method according to aspect 1, characterized in that a filtration step is carried out in step b) before adding an acid.

Aspect 3

The method according to aspect 1 or 2, characterized in that, after step d), the sample is degassed at reduced pressure.

Aspect 4

A method according to at least one of aspects 1 to 3, characterized in that, in step d), the sample is adjusted to a ph value of 5 to 6.

Aspect 5

A method according to at least one of aspects 1 to 4, characterized in that the plasma sample originates from a subject or patient who took $^{13}C$-labeled urea precursors before the collection.

Aspect 6

A method for determining the $^{13}C$ isotope ratio of urea in a plasma sample, comprising the steps of isolating urea by way of a method according to any one of aspects 1 to 5, rinsing with inert gas, adding urease so as to produce $CO_2$, incubating, adding an acid so as to release the $CO_2$ that has been produced, and measuring the $^{13}C$ isotope ratio of the released $CO_2$.

Aspect 7

A method for diagnosing urea metabolism, comprising the steps of providing a first plasma sample of a patient, determining the $^{13}C$ isotope ratio of urea in the first plasma sample according to aspect 6, providing at least one additional plasma sample originating from the patient, wherein the patient took $^{13}C$-labeled urea precursors before the collection, determining the $^{13}C$ isotope ratio of urea in the at least one additional plasma sample according to aspect 6, and quantifying the amount of the urea that has been produced by way of the $^{13}C$ isotope ratio of the urea in the first and the at least one additional plasma samples.

Aspect 8

The method according to aspect 7, characterized in that at least two additional plasma samples are used.

Aspect 9

The method according to aspect 8, characterized in that the additional plasma samples were collected over a period of 15 to 240 minutes after the patient took $^{13}C$-labeled urea precursors.

Aspect 10

The method according to either aspect 8 or 9, characterized in that the additional plasma samples were collected at intervals of 15 minutes after the patient took $^{13}C$-labeled urea precursors.

The present invention relates in particular also to the following aspects: A), B), C), D), E), F), G), H), I):

Aspect A

A method for determining urea in plasma samples, comprising the following steps: a) providing a plasma sample containing urea; b) adding an acid; c) lyophilizing the sample so as to remove $CO_2$ and obtain a dried sample; d) redissolving the dried sample and neutralizing to a pH value of 5 to 7 using a buffer solution; e) rinsing with inert gas; f) adding urease so as to produce $CO_2$; g) incubating; h) adding an acid so as to release the $CO_2$ that has been produced; and i) determining the isotope ratio of the released $CO_2$.

Aspect B

The method according to aspect A), characterized in that a filtration step is carried out before lyophilizing.

Aspect C

The method according to aspect A) or B), characterized in that, after step d), the sample is heated to a temperature between 40 and 70° C.

Aspect D

A method according to at least one of aspects A) to C), characterized in that IRMS is employed to determine the isotope ratio of the $CO_2$.

Aspect E

A method according to at least one of aspects A) to D), characterized in that 13C-labeled acetate is administered before collecting a plasma sample.

Aspect F

A method according to at least one of aspects A) to E), characterized in that, in step d), the sample is adjusted to a pH value of 5 to 6.

Aspect G

A method for diagnosing urea metabolism, comprising the steps of collecting a blood sample from a patient, obtaining a plasma sample from the blood sample, determining the urea in the plasma sample by way of the method according to any one of aspects A) to F), administering a 13C-labeled urea precursor, collecting at least two blood samples with time lag from each other, and determining the urea after obtaining plasma samples from the blood samples by way of a method according to any one of aspects A) to F).

Aspect H

The method according to aspect G), characterized in that, after the urea precursors have been administered, the at least two blood samples are collected over a period of at least 120 minutes, preferably at least 240 minutes.

Aspect I

The method according to aspect G or H), characterized in that a time period of 10 to 20 minutes exists between two collections of blood samples.

DETAILED DESCRIPTION OF THE INVENTION

The method will be described in more detail by way of the following examples.

Example 1: Urea Isolation Using Filtration

Plasma was obtained from a blood sample. 300 µl plasma was diluted with 200 µl deionized water. 100 µl acetonitrile containing 1% formic acid was added to the sample. A precipitation formed in the vessel. The samples were filtered using a HybridSPE column.

The filtrate was mixed with 50 µl M phosphoric acid, frozen and lyophilized. The sample was adjusted to a pH value of 5.5 using a degassed 0.5 M phosphate buffer solution, pH 9. The sample container (Vacutainer) was rinsed with helium gas. Thereafter, 70 µl of a solution containing 15 mg/ml Jack Bean Urease Type III from Sigma in phosphate buffer was added. The sample was incubated for one hour at 36° C. Thereafter, 60 µl 20% phosphoric acid was injected through the septum so as to stop the urease reaction and release $CO_2$. The released $CO_2$ was used to determine the isotope ratio by means of IRMS.

Example 2: Urea Isolation Using No Filtration

The method as in Example 1 was carried out, however the addition of acetonitrile and formic acid, and the filtration step were dispensed with, which is to say the plasma sample was directly lyophilized after acid was added. The remainder of the method was carried out in identical fashion.

Example 3: Reproducibility of the Method

Figure 1:
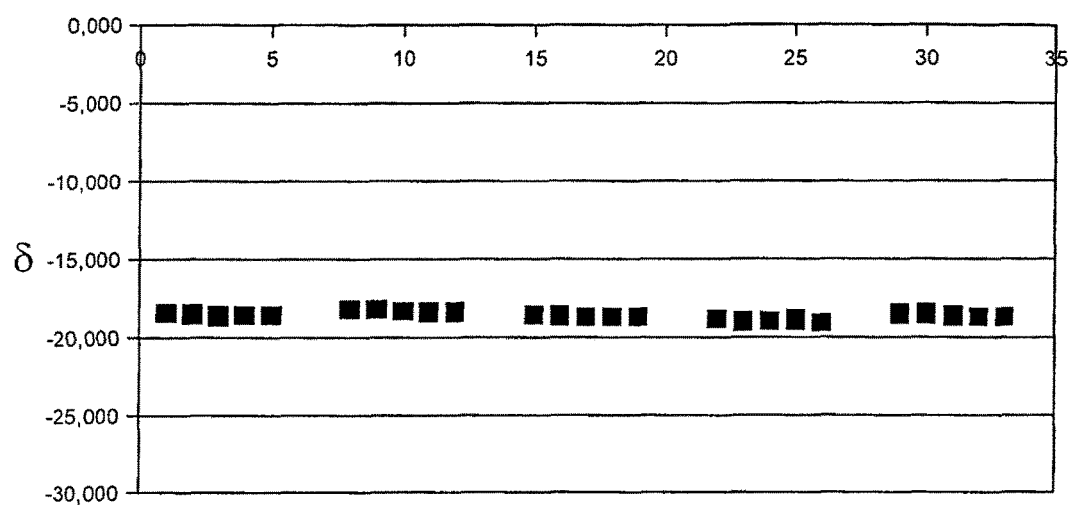
FIG. 1 shows the reproducibility of the method according Example 3.

A plasma sample was divided into five samples, which were each subjected separately from each other to the method according to Example 1. Each $CO_2$ sample that was obtained was measured five times. The differences are minimal; refer to FIG. 1.

Example 4: Spiking Experiment

Figure 2:
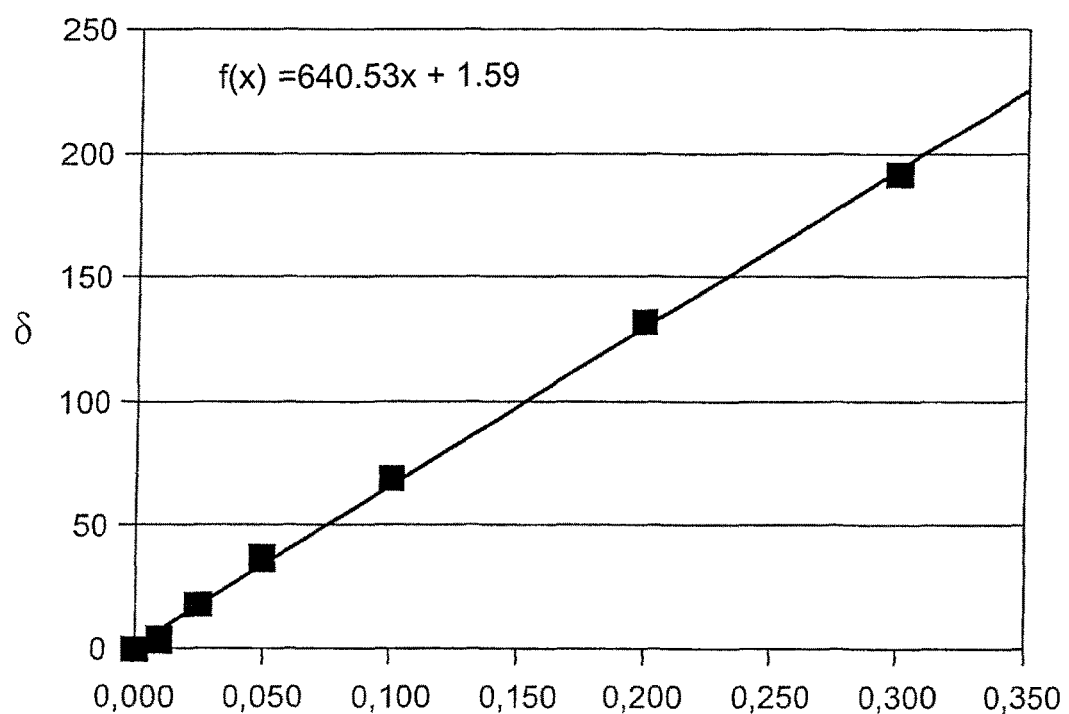
FIG. 2 shows the calibration curve of the spiking experiment according to Example 4.

99% labeled $^{13}C$ urea was added to the plasma samples from Example 1 in quantities of 0.01 mg, 0.25 mg, 0.5 mg, 0.1 mg, 0.2 mg, and 0.3 mg, and the sample was treated in accordance with method 1. FIG. 2 shows the corresponding measurement values. The calibration curve is located on a straight line with a correlation coefficient of 0.99923.

Example 5: Reproducibility

Figure 3:
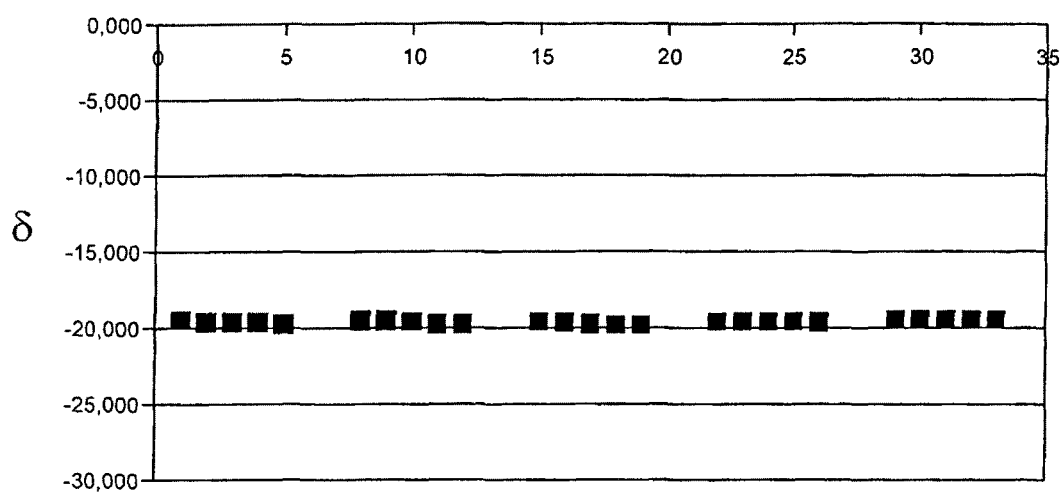
FIG. 3 shows the reproducibility of the method according to Example 5.

The measurement regarding reproducibility according to Example 3 was repeated for the method using no filter according to Example 2. FIG. 3 shows the results. Again, excellent reproducibility exists.

Example 6: Spiking Experiment

Figure 4:
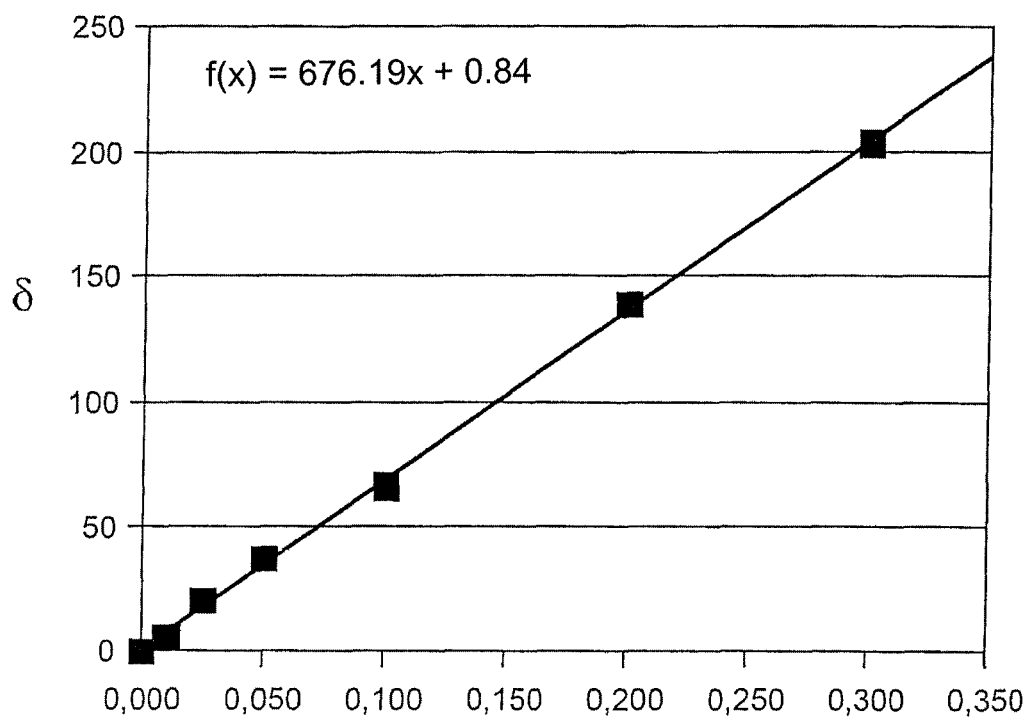
FIG. 4 shows the calibration curve of the spiking experiment according to Example 6.

The spiking experiment according to Example 4 was repeated, wherein the method according to Example 2 was employed. The corresponding straight calibration line is apparent from FIG. 4. The coefficient of correlation thereof was R=0.99959.

Example 7: Measurement of the Urea Production

Blood was collected from two subjects, and from 300 µl of the plasma that was obtained from each of the blood samples, urea was isolated using the method according to the invention, and the $^{13}C/^{12}C$ isotope ratio of the urea was determined.

Each sample was measured 5 times and the basal value was determined by way of the average value. The subjects were then administered 27 mg/kg 99% $^{13}C$-labeled Na-acetate.

Figure 5:
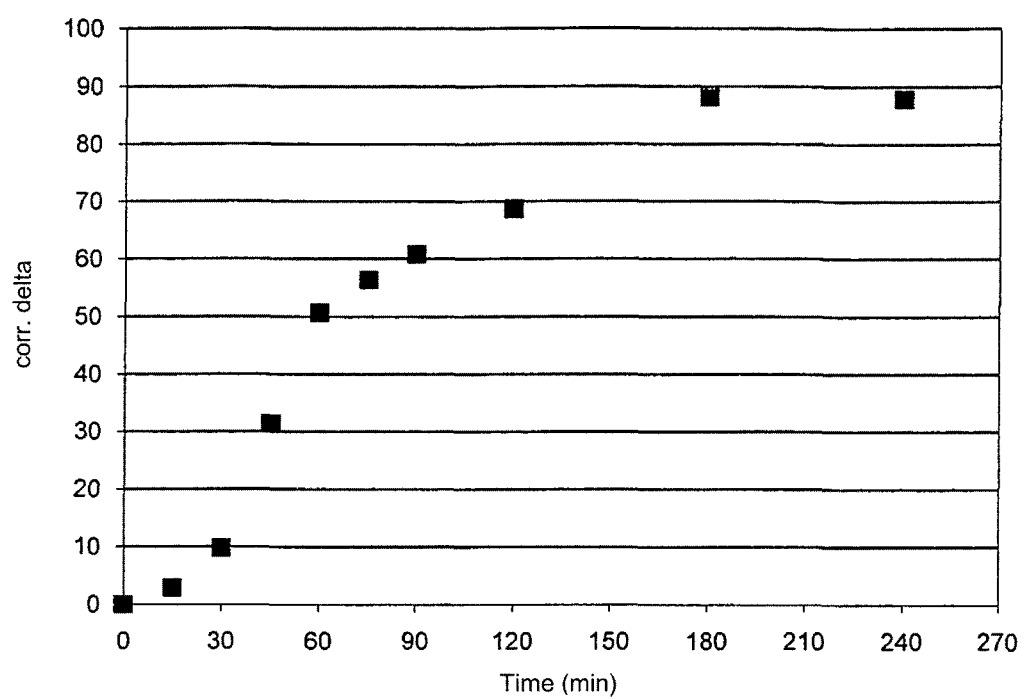
FIGS. 5 and 6 show the results of the measurement of the urea production according to Example 7.
Figure 6:
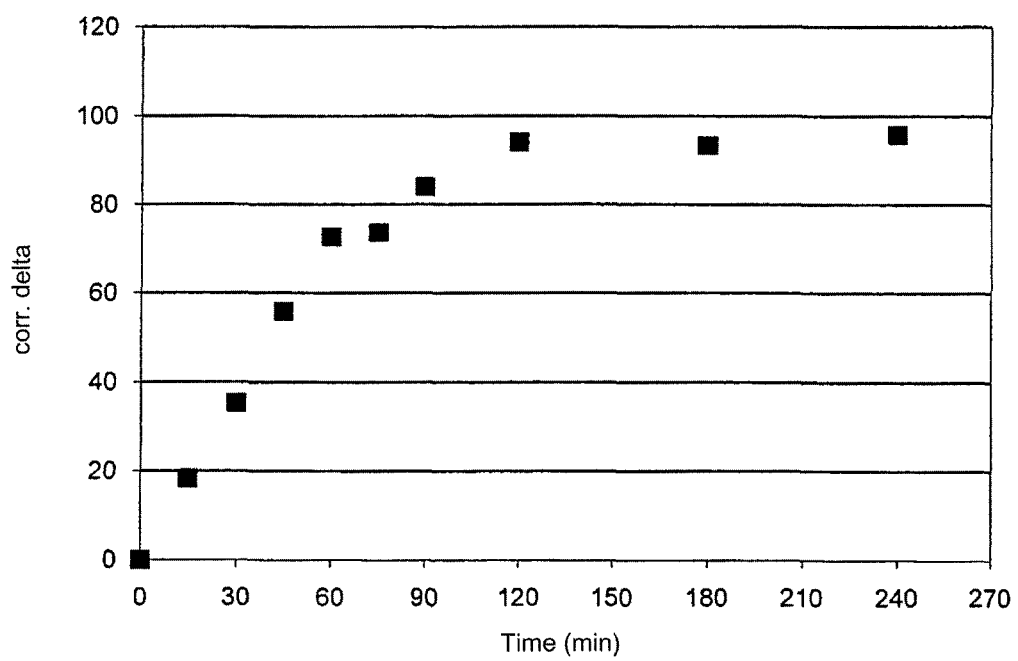

The procedure of collecting blood and determining the $^{13}C/^{12}C$ isotope ratio of the isolated urea was repeated at 15-, 30-, 45-, 60-, 75-, 90-, 120-, 180-, and 240-minute intervals. A smaller portion of the $^{13}C$-labeled acetate is converted into urea in the body and can be detected because of the sensitivity of the measurement. The kinetics of the newly produced urea was determined by measuring the delta values (increasing the $^{13}C/^{12}C$ isotope ratio). The kinetics of the urea production is shown in FIGS. 5 and 6.

The invention claimed is:

1. A method for determining the $^{13}C$ isotope ratio of urea in a plasma sample, comprising the following steps in the following order:
   a) collecting a plasma sample from a person to whom a $^{13}C$-labeled urea precursor has been administered;
   b) precipitating material comprising proteins and lipids from the plasma sample, then separating the precipitated material from the plasma sample by filtration, and then adding an acid to the plasma sample, whereby $CO_2$ is partially removed from the plasma sample;
   c) lyophilizing the sample treated in step b), whereby residual $CO_2$ is removed from the sample and a dried sample is obtained;
   d) redissolving the dried sample, thereby obtaining a sample solution, neutralizing the sample solution with a buffer solution to a pH value of 5 to 6;
   e) degassing the sample solution at reduced pressure to remove $CO_2$ introduced into the sample solution by the buffer solution so that as a result of steps b) through e), the sample solution is $CO_2$-free as determined by isotope ratio mass spectrometry (IRMS);
   f) rinsing the sample solution with inert gas;
   g) adding urease to the rinsed sample solution so as to produce $CO_2$;
   h) incubating the sample solution after urease has been added thereto;
   i) adding an acid to the incubated sample solution so as to release $CO_2$ that has been produced in the incubated sample solution; and
   j) measuring the $^{13}C$ isotope ratio of the released $CO_2$.

2. The method according to claim 1, wherein, in steps b) and i), the acid is phosphoric acid.

3. A method according to claim 1, wherein, in step d), the buffer solution is phosphate buffer solution having a pH of 9.0.

4. The method according to claim 1, wherein the plasma sample collected in step a) is of a volume of 0.3 ml, and in step g), 20 to 100 units of the urease are added to the rinsed sample solution.

5. A method for diagnosing urea metabolism in a person, comprising: determining, for each of a plurality of plasma samples collected from the person, the $^{13}C$ isotope ratio in the plasma sample by the method of claim 1, wherein each of the blood samples collected after a first of the blood samples is collected, is collected at a predetermined time interval after the previous blood sample has been collected.

6. The method according to claim 5, wherein the plasma samples are collected over a time period of 15 to 240 minutes.

7. The method according to claim 5, wherein the predetermined time interval is 15 minutes.

8. The method according to claim 1, wherein the plasma sample collected in step a) is of a volume 0.2 to 0.3 ml.

9. The method according to claim 1, wherein the degassing of the sample solution in step e) is effected by applying to the sample solution for 2 to 3 hours a vacuum in a range of 1 to 10 mbar.

\* \* \* \* \*